United States Patent

Kröck et al.

[11] 4,264,511
[45] Apr. 28, 1981

[54] ANTHRAQUINONE COMPOUNDS

[75] Inventors: Friedrich W. Kröck, Cologne; Rütger Neeff, Leverkusen, both of Fed. Rep. of Germany

[73] Assignee: Bayer Aktiengesellschaft, Leverkusen, Fed. Rep. of Germany

[21] Appl. No.: 38,064

[22] Filed: May 11, 1979

[30] Foreign Application Priority Data

May 13, 1978 [DE] Fed. Rep. of Germany ....... 2821148

[51] Int. Cl.³ .......................................... C07C 143/665
[52] U.S. Cl. ......................................... 260/373; 8/676
[58] Field of Search ..................... 260/371, 373; 8/675, 8/676

[56] References Cited

U.S. PATENT DOCUMENTS

| 2,394,918 | 2/1946 | Kienle et al. | 260/371 |
| 2,938,914 | 5/1960 | Joyce | 260/371 |
| 3,549,664 | 12/1970 | Groll et al. | 260/371 |
| 4,041,051 | 8/1977 | Yamada et al. | 260/371 |

FOREIGN PATENT DOCUMENTS 1176777  8/1964  Fed. Rep. of Germany .

OTHER PUBLICATIONS

*Organic Chemistry*, 3rd Ed. p. 527, Morrison & Boyd, 1973, copy in Group 110.

*Primary Examiner*—Winston A. Douglas
*Assistant Examiner*—Raymond K. Covington
*Attorney, Agent, or Firm*—Sprung, Felfe, Horn, Lynch & Kramer

[57] ABSTRACT

New anthraquinone compounds of the formula

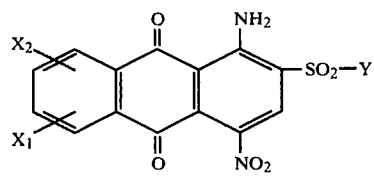

in which
Y denotes chlorine, bromine, —O—R or

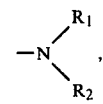

R denotes aryl,
$R_1$ and $R_2$ denote hydrogen, alkyl, cycloalkyl or aryl and
$X_1$ and $X_2$ denote hydrogen, halogen or nitro, are obtained when the corresponding 2-sulphonic acids are treated with inorganic acid halides and the products are then optionally treated with alcohols or amines. The compounds I are valuable dyestuffs for dyeing polyester fibres and starting materials for the preparation of such dyestuffs.

12 Claims, No Drawings

ANTHRAQUINONE COMPOUNDS

The present invention relates to new anthraquinone dyestuffs of the formula

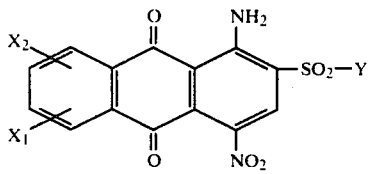  I in which
Y denotes a group of the formulae —O—R or

,

R denotes optionally substituted aryl,
$R_1$ and $R_2$ denote hydrogen or optionally substituted alkyl, cycloalkyl, aralkyl or aryl, or, together with the bonding nitrogen atom, a ring and
$X_1$ and $X_2$ denote hydrogen, halogen or nitro,
the process for their preparation, their use for dyeing synthetic materials, and intermediate products, for the preparation of these dyestuffs, of the formula

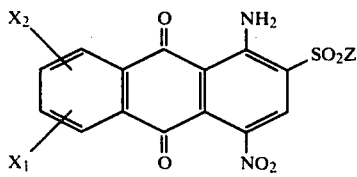  II in which
$X_1$ and $X_2$ have the abovementioned meaning and
Z represents chlorine or bromine,
and the preparation thereof.

Suitable aryl radicals R, $R_1$ and $R_2$ are naphthyl radicals and, in particular, phenyl radicals, which can contain the substituents customary in dyestuff chemistry, for example those of the type indicated below.

Suitable alkyl radicals $R_1$ and $R_2$ are straight-chain or branched, contain 1 to 10 carbon atoms and can be substituted by halogen, hydroxyl, $C_1$- to $C_4$-alkoxy, phenoxy, amino, $C_1$- to $C_4$-alkylamino, $C_1$- to $C_4$-dialkylamino, cyano, $C_1$- to $C_4$-alkoxy-carbonyl or $C_5$- to $C_6$-cycloalkyl and the trifluoromethyl radical. Suitable cycloalkyl radicals $R_1$ and $R_2$ are those with 5 to 6 carbon atoms and can carry 1 to 3 substituents, such as halogen, hydroxyl, cyano or $C_1$- to $C_4$-alkyl.

Suitable aralkyl radicals $R_1$ and $R_2$ are those which contain 1 to 4 carbon atoms in the alkylene radical and in which the aryl radical is a naphthyl radical and, in particular, a phenyl radical, which is optionally monosubstituted, disubstituted or trisubstituted by halogen, $C_1$- to $C_4$-alkyl or $C_1$- to $C_4$-alkoxy.

By halogen there is understood fluorine, bromine and, above all, chlorine. Preferred ;yestuffs are those of the formula I wherein Y represents OR, R denoting a phenyl radical which is optionally substituted by 1 to 3 radicals from the series $C_1$- to $C_4$-alkyl, $C_1$- to $C_4$-alkoxy, halogen, such as, in particular, fluorine, chlorine and bromine, methylmercapto, nitro, trifluoromethyl, $C_5$- to $C_6$-cycloalkyl, phenyl, acetyl, benzoyl, carbomethoxy or carboxyl, or a naphthyl or 5,6,7,8-tetrahydronaphthyl radical which is optionally substituted by methyl, chlorine or bromine.

Furthermore, those dyestuffs of the formula I wherein Y represents $-NR_1R_2$, $R_1$ and $R_2$ denoting hydrogen, $C_1$- to $C_6$-alkyl which is optionally substituted by hydroxyl, $C_1$- to $C_4$-alkoxy, cyano or cyclohexyl, cyclohexyl which is optionally substituted by 1 to 3 methyl radicals or by cyano, benzyl, phenethyl or naphthylmethyl, optionally monosubstituted, disubstituted or trisubstituted by halogen, methyl or methoxy, phenyl which is substituted by 1 to 3 radicals from the series $C_1$- to $C_4$-alkyl, $C_1$- to $C_4$-alkoxy, chlorine, fluorine, bromine, nitro, trifluoromethyl, $C_5$- to $C_6$-cycloalkyl, phenyl or acetyl, or naphthyl or 5,6,7,8-tetrahydronaphthyl, optionally substituted by methyl, chlorine or bromine, and those in which $R_1$ and $R_2$, together with the bonding nitrogen atom, represent $-(CH_2)_4-$, $-(CH_2)_5-$ or $-(CH_2)_2-O-(CH_2)_2-$ are preferred.

From the last group, those dyestuffs in which one of the radicals $R_1$ and $R_2$ represents hydrogen or in which $R_1$ and $R_2$ both represent $C_1$- to $C_6$-alkyl which is optionally substituted as above are very particularly preferred.

$X_1$ and $X_2$ preferably represent hydrogen.

"Bulky" radicals are preferably in those positions where they cause no steric hindrance.

The new dyestuffs are obtained, for example, when anthraquinonesulphonic acid halides of the formula II are reacted with phenols of the formula ROH, in which R has the abovementioned meaning,
or with amines of the formula

in which $R_1$ and $R_2$ have the abovementioned meaning, in a manner which is in itself known.

Examples of the anthraquinonesulphonic acid halides II used as the starting material are, in particular, the corresponding anthraquinonesulphonic acid chlorides, such as the following: 1-amino-4-nitro-anthraquinone-2-sulphonic acid chloride, 1-amino-4-nitro-5-chloro-anthraquinone-2-sulphonic acid chloride, 1-amino-4-nitro-6-chloro-anthraquinone-2-sulphonic acid chloride, 1-amino-4-nitro-7-chloro-anthraquinone-2-sulphonic acid chloride, 1-amino-4-nitro-6,7-dichloro-anthraquinone-2-sulphonic acid chloride, 1-amino-4-nitro-6-fluoro-anthraquinone-2-sulphonic acid chloride, 1-amino-4-nitro-7-fluoro-anthraquinone-2-sulphonic acid chloride, 1-amino-4-nitro-6,7-difluoro-anthraquinone-2-sulphonic acid chloride, 1-amino-4,5-dinitro-anthraquinone-2-sulphonic acid chloride, 1-amino-4,6-dinitro-anthraquinone-2-sulphonic acid chloride, 1-amino-4,7-dinitro-anthraquinone-2-sulphonic acid chloride and 1-amino-4,8-dinitro-anthraquinone-2-sulphonic acid chloride, and the corresponding sulphonic acid bromides, in particular 1-amino-4-nitro-anthraquinone-2-sulphonic acid bromide.

The following compounds are examples of the phenols ROH used as starting materials: phenol, p-chlorophenol, m-chlorophenol, o-chlorophenol, p-bromophenol, o-, m- and p-cresol, 2,4-dichlorophenol, 3,4-dimethylphenol, 3-chloro-6-methylphenol, p-methylmercaptophenol, m-methoxyphenol, p-methoxyphenol, p-acetylphenol, 3-hydroxybenzoic acid, 4-hydroxybenzoic acid methyl ester, p-trifluoromethylphenol, 3-nitrophenol, 4-cyclohexyl-phenol, 4-phenyl-phenol, 4-hydroxy-benzophenone, α-naphthol, β-naphthol and 5,6,7,8-tetrahydro-1-naphthol.

The following compounds are examples of the amines

used as starting materials: ammonia, methylamine, ethylamine, isopropylamine, n-propylamine, n-butylamine, isobutylamine, tert.-butylamine, n-pentylamine, n-hexylamine, decylamine, dimethylamine, diethylamine, dipropylamine, dibutylamine, 2-hydroxy-ethylamine, 2-methoxy-ethylamine, 2-ethoxy-ethylamine, 2-butoxyethylamine, 2-cyano-ethylamine, 2-chloro-ethylamine, 2-methylamino-ethanol, bis-(2-hydroxy-ethyl)-amine, 1-amino-2-propanol, 2,3-dihydroxy-propylamine, 2-phenoxy-ethylamine, 1,2-diamino-ethane, N,N-dimethyl-1,2-diaminoethane, 3-hydroxy-propylamine, 3-methoxy-propylamine, N,N-dimethyl-1,3-diamino-propane, aminoacetic acid methyl ester, aminoacetic acid ethyl ester, cyclopentylamine, cyclohexylamine, 4-cyano-cyclohexylamine, 4-methyl-cyclohexylamine, 3-methyl-cyclohexylamine, 3,3,5-trimethyl-cyclohexylamine, N-methyl-cyclohexylamine, amino-methylcyclohexane, benzylamine, 4-chloro-benzylamine, 3- and 4-methyl-benzylamine, 3- and 4-methoxy-benzylamine, β-phenethylamine, aniline, 4-chloro-aniline, 3-chloro-aniline, 2-chloro-aniline, 4-bromo-aniline, 2-methyl-aniline, 3-methyl-aniline, 4-methyl-aniline, 2,4-dimethyl-aniline, 2,4-dichloroaniline, 2,5-dichloroaniline, 4-hydroxy-aniline, 4-methoxy-aniline, 3-methoxy-aniline, anthranilic acid, anthranilic acid methyl ester and ethyl ester, 4-trifluoromethyl-aniline, 3-trifluoromethyl-aniline, 3-nitroaniline, 4-cyclohexyl-aniline, 4-amino-diphenyl, α-naphthylamine, 1-amino-5,6,7,8-tetrahydro-naphthalene, 2-amino-5,6,7,8-tetrahydro-naphthalene, 1-amino-1,2,3,4-tetrahydro-naphthalene and 2-amino-1,2,3,4-tetrahydro-naphthalene.

The reaction of the anthraquinonesulphonic acid halides II with phenols of the formula ROH or amines of the formula

can be carried out in an aqueous medium or in an organic solvent, the reaction generally being carried out with the addition of an acid-binding agent. Suitable acid-binding agents are inorganic bases, such as, for example, oxides or hydroxides of alkali metals or alkaline earth metals, such as sodium hydroxide, potassium hydroxide or calcium oxide, or alkali metal salts of weak acids, such as sodium carbonate, potassium carbonate, sodium acetate or potassium acetate, or organic bases, such as, for example, trimethylamine, triethylamine or benzyltrimethyl-ammonium hydroxide. If the reaction is carried out with amines of the formula

if appropriate, an additional acid-binding agent can be dispensed with and the amine can be employed in excess.

Examples of organic solvents which may be mentioned are: toluene, chlorobenzene, 1,2-dichlorobenzene, nitrobenzene, dioxane, tetrahydrofurane, dimethylformamide, dimethylsulphoxide, tetramethylene sulphone (sulpholane), pyridine, diglycol monomethyl ether, glycol dimethyl ether, acetone and methyl ethyl ketone.

The reaction can be carried out at room temperature or at higher or lower temperatures, for example between $-20°$ and $+100°$ C., preferably at $0°$ to $60°$ C.

The new dyestuffs of the formula I and mixtures thereof with one another and mixtures with suitable known dyestuffs are outstandingly suitable for dyeing and printing synthetic fibre materials of cellulose esters, polyamides, polyurethanes, polyacrylonitriles and aromatic polyesters, in particular polyethylene glycol terephthalates, by conventional dyeing processes.

The dyeing or printing can be carried out by processes which are in themselves known for dyeing from an aqueous liquor, either with the pure dyestuffs or with mixtures of two or more dyestuffs. It is advantageous to convert the dyestuffs or the dyestuff mixtures into a finely divided state before using them in accordance with customary methods.

Furthermore, the new dyestuffs are suitable for dyeing the types of fibre mentioned from water-immiscible organic solvents by the exhaustion process, such as is described, for example, in British Pat. Nos. 1,314,022 and 1,284,670 (=U.S. Pat. No. 3,792,971). Tetrachloroethylene is the preferred solvent.

Moreover, the new dyestuffs are outstandingly suitable for dyeing mixed fabrics of synthetic and natural fibre materials, preferably those of polyester and cellulose (especially cotton) and polyester and wool.

The new water-insoluble dyestuffs can also be used for spin-dyeing polyamides, polyesters and polyolefins. The polymer to be dyed is appropriately mixed, in the form of powders, granules or chips, as the finished spinning solution or in the molten state, with the dyestuff, which is introduced in the dry state or in the form of a dispersion or solution in an appropriately volatile solvent. After homogeneous distribution of the dyestuff in the solution or melt of the polymer, the mixture is processed in a known manner by casting, moulding or extruding to give fibres, yarns, monofilaments, films and the like.

The dyeings produced on the types of fibre mentioned are distinguished by good general fastness properties.

The present invention also relates to the anthraquinonesulphonic acid halides of the formula II, which are obtained, for example, when anthraquinonesulphonic acids of the formula

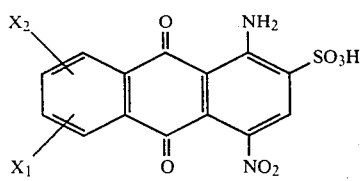

in which $X_1$ and $X_2$ have the abovementioned meaning, or salts thereof are treated with appropriate inorganic acid halides, and when the sulphonic acid chlorides thus obtained are converted into the sulphonic acid bromides in a manner which is in itself known.

Some of the anthraquinonesulphonic acids III used as the starting material are known (compare DOS (German Published Specification) No. 1,906,834 or Swiss Application No. 2468-68 and DAS (German Published Specification) No. 1,176,777, Example 7) or they can be prepared by known processes.

Examples of suitable inorganic acid halides are chlorosulphonic acid, thionyl chloride, phosphorus trichloride, phosphorus oxychloride, phosphorus pentachloride, thionyl bromide, phosphorus tribromide, phosphorus pentabromide and phosphorus oxybromide.

Phosphorus oxychloride is preferred for the preparation of the sulphonic acid chlorides according to formula II.

The reaction of the anthraquinonesulphonic acids III with inorganic acid halides can be carried out by processes which are known in principle, in a suitable solvent or in an excess of the inorganic acid halide itself.

Examples of suitable solvents which may be mentioned are, in particular: toluene, chlorobenzene, 1,2-dichlorobenzene, 1,2,4-trichlorobenzene, nitrobenzene, dioxane, tetrahydrofurane, dimethylformamide, dimethylsulphoxide, tetramethylenesulphone (sulpholane), glycol dimethyl ether, chloroform and 1,2-dichloroethane.

Depending on the reactivity of the inorganic acid halide employed, the reaction can be carried out at room temperature or at higher or lower temperatures, for example between 0° and 150° C., preferably at 40° to 120° C. The procedure is, for example, to initially introduce the excess inorganic acid halide, to add, at room temperature, the thoroughly dried alkali metal salt of the sulphonic acid III to be reacted and to bring the mixture to the required temperature, or to add the alkali metal salt of the sulphonic acid III to the initially introduced inorganic acid chloride at the reaction temperature. When the reaction has ended, the sulphonic acid halide formed can be isolated in various ways. It is possible, for example, to cool the reaction mixture, if appropriate after all or some of the inorganic acid halide has been distilled off, and to separate off the sulphonic acid halide, which has crystallised out directly or after dilution with a suitable inert solvent. Another possibility is to cool the reaction mixture, if appropriate after all or some of the inorganic acid halide has been distilled off, and to discharge it into ice-water, to stir the mixture at a maximum temperature of 25° C. until complete decomposition of the excess inorganic acid halide has taken place, and then to separate off the sulphonic acid halide of the formula II, which has precipitated. If the reaction is carried out in an inert solvent, it can be more appropriate, in the case of a water-immiscible solvent, to remove some or all of the solvent by distillation, if appropriate in vacuo, and then to cause the sulphonic acid halide to crystallise by stirring the residue in water or by adding another suitable solvent.

If the reaction is carried out in chlorosulphonic acid, the procedure can be as described in DAS (German Published Specification) No. 1,271,284, and the sulphonic acids or salts thereof can be stirred in excess chlorosulphonic acid at room temperature until the starting material has reacted completely. However, it is usually more favourable to carry out the preparation of the sulphonic acid chloride in a mixture of chlorosulphonic acid and thionyl chloride according to the statements of DOS (German Published Specification) No. 2,356,776, or to carry out the preparation in a mixture of thionyl chloride and sulphur trioxide according to the statements of DOS (German Published Specification) No. 2,635,281 (=Belgian Pat. No. 857,498).

The procedure for the preparation of the sulphonic acid bromide can also be to convert the sulphonic acid chloride into the sulphonic acid bromide in a manner which is in itself known, for example by treatment with an alkali metal bromide or alkaline earth metal bromide, in particular with lithium bromide or calcium bromide, in a suitable anhydrous organic solvent, such as, in particular, acetone or an alcohol, such as, for example, ethanol, at room temperature or if appropriate at an elevated temperature, up to the boiling point of the reaction mixture (compare, for example, Organikum, pages 197–198; 5th edition).

EXAMPLE 1

185 g of thoroughly dried sodium 1-amino-4-nitroanthraquinone-2-sulphonate, prepared according to the instructions in DOS (German Published Specification) No. 1,906,834, Example 1 or Example 2, are introduced in portions into 1,240 g (=740 ccs) of phosphorus oxychloride at 100° C. The mixture is kept at 100° C., whilst stirring, until the starting material has disappeared without trace according to the thin layer chromatogram, after about 2 hours, and a solution has formed. After cooling, the reaction mixture is poured into 7 l of ice-water in a manner such that the temperature does not exceed 20° C. and the mixture is stirred until the phosphorus oxychloride has decomposed completely, after about 1 hour, and the sulphonic acid chloride of the formula

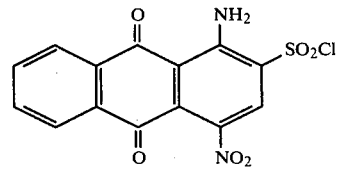

has precipitated and the precipitate is filtered off and washed with cold water until neutral. The product is dried in vacuo over sodium hydroxide. Yield: 174.5 g, corresponding to 95% of theory; melting point: about 250° C. (decomposition).

Analysis: $C_{14}H_7ClN_2O_6S$ (366.7). Calculated: C 45.85; H 1.92; N 7.64; Cl 9.68; S 8.74. Found: C 46.1; H 1.8; N 7.6; Cl 9.9; S 8.8.

Instead of pouring the reaction mixture into water, it can be also be worked up as follows:

(a) The solution is cooled to 0° to 5° C. in an ice-bath for 2 hours and the crystals which have precipitated are then filtered off on a glass frit and introduced into ice-water, the mixture is stirred for 1 hour and the crystals are again filtered off, washed until neutral and dried in vacuo over sodium hydroxide. Yield: 132 g, corresponding to 72% of theory; melting point: about 250° C. (decomposition).

(b) About 400 ccs of phosphorus oxychloride are distilled off from the resulting reaction mixture in vacuo. The residue is cooled to 0° to 5° C. in an ice-bath for 2 hours. The crystals which have precipitated are then filtered off with good suction, stirred with 1.5 l of water for 1 hour at a maximum temperature of 20° C., filtered off again, washed with cold water until neutral and dried as above. Yield: 173 g, corresponding to 94% of theory.

The phosphorus oxychloride recovered can be used again for the preparation of the sulphonic acid chloride.

(c) About 400 ccs of phosphorus oxychloride are distilled off from the resulting reaction mixture as above. The residue is poured into 2.5 l of ice-water and the mixture is stirred at a maximum temperature of 20° C. for 1 hour, until the phosphorus oxychloride has decomposed. The sulphonic acid chloride which has precipitated is filtered off, washed and dried, as above. Yield: 176 g, corresponding to 96% of theory.

The phosphorus oxychloride recovered can be used again for the preparation of the sulphonic acid chloride.

(d) The sulphonic acid chloride is also obtained in a similar yield and purity if phosphorus trichloride or phosphorus pentachloride is used instead of phosphorus oxychloride.

EXAMPLE 2

37 g of thoroughly dried sodium 1-amino-4-nitro-anthraquinone-2-sulphonate are suspended in 300 ccs of toluene, the suspension is heated to 100° C. and 48 g of phosphorus oxychloride are added dropwise thereto at this temperature. The mixture is kept at this temperature for about 20 hours, the unreacted, undissolved starting material is filtered off, the toluene is then distilled off in vacuo and the residue is extracted by stirring in 500 ccs of water at a maximum temperature of 20° C. for about 1 hour. The sulphonic acid chloride is then filtered off, washed until neutral and dried as in Example 1. Yield: 33 g, corresponding to 90% of theory.

As the melting point and mixed melting point show, the same product as described in Example 1 is obtained.

The sulphonic acid chloride is obtained in a similar yield and purity if chlorobenzene, 1,2-dichlorobenzene, 1,2,4-trichlorobenzene, nitrobenzene, dioxane, tetrahydrofurane, dimethylformamide, dimethylsulphoxide, tetramethylene sulphone, glycol dimethyl ether, chloroform or 1,2-dichloroethane is used instead of toluene.

EXAMPLE 3

18.5 g of thoroughly dried sodium 1-amino-4-nitro-anthraquinone-2-sulphonate are introduced into 76 g (=43 ccs) of chlorosulphonic acid, and 22.5 g (=13.5 ccs) of thionyl chloride are added dropwise to the mixture at 20° to 25° C. in the course of 60 minutes. When all of the starting material has reacted, after about 3 hours, the mixture is poured onto 750 ccs of ice-water and the sulphonic acid chloride which has precipitated is filtered off, washed until neutral and dried as described in Example 1. Yield: 17 g, corresponding to 92% of theory.

The sulphonic acid chloride is obtained in a similarly good yield and purity if the reaction is carried out according to the instructions in DOS (German Published Specification) No. 2,635,281 (=Belgian Pat. No. 857,498) in excess thionyl chloride in the presence of catalytic amounts of sulphur trioxide or chlorosulphonic acid.

EXAMPLE 4

55.5 g of phosphorus pentabromide and 18.5 g of thoroughly dried sodium 1-amino-4-nitro-anthraquinone-2-sulphonate are introduced into 200 ccs of tetrahydrofurane. The mixture is kept at 100° C., whilst stirring, until the starting material has reacted according to the thin layer chromatogram, and the reaction mixture is cooled and poured into 1 liter of ice-water. After stirring the mixture at 0°-5° C. for 1 hour, the precipitate is filtered off, washed until neutral and dried. Yield: 17 g, corresponding to 82% of theory, of the product of the formula

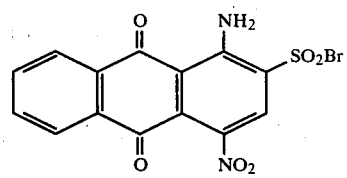

the structure of which is confirmed by analyses and the mass spectrum. The reaction can also be carried out with phosphorus tribromide, phosphorus oxybromide or thionyl bromide instead of with phosphorus pentabromide. Likewise, it is also possible to use dioxane, toluene, chlorobenzene or dimethylformamide instead of tetrahydrofurane. If toluene or chlorobenzene is used, the solvent must be distilled off before introducing the reaction mixture into water.

Instead of being obtained from the sulphonic acid, the sulphonic acid bromide can also be obtained by a chlorine replacement reaction from the sulphonic acid chloride, which has been obtained according to one of the preceding examples. The reaction can be carried out with, for example, lithium bromide or calcium bromide in acetone or ethanol.

EXAMPLES 5–21

The sulphonic acid chlorides and bromides listed in Table 1, the structure of which is confirmed by analyses and mass spectra on the one hand and by their reaction products with phenols and amines on the other hand, can also be prepared according to the instructions of Examples 1 to 4.

TABLE 1

| Example No. | Y | $X_1$ | $X_2$ |
|---|---|---|---|
| 5 | Cl | 5-Cl | H |
| 6 | Cl | 6-Cl | H |
| 7 | Cl | 7-Cl | H |
| 8 | Cl | 8-Cl | H |
| 9 | Cl | 5-Cl | 8-Cl |
| 10 | Cl | 6-Cl | 7-Cl |
| 11 | Cl | 6-F | H |
| 12 | Cl | 7-F | H |
| 13 | Cl | 6-F | 7-F |
| 14 | Cl | 5-$NO_2$ | H |
| 15 | Cl | 6-$NO_2$ | H |

TABLE 1-continued

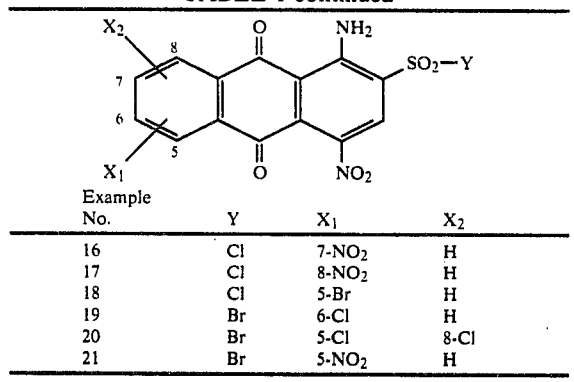

| Example No. | Y | $X_1$ | $X_2$ |
|---|---|---|---|
| 16 | Cl | 7-$NO_2$ | H |
| 17 | Cl | 8-$NO_2$ | H |
| 18 | Cl | 5-Br | H |
| 19 | Br | 6-Cl | H |
| 20 | Br | 5-Cl | 8-Cl |
| 21 | Br | 5-$NO_2$ | H |

EXAMPLE 22

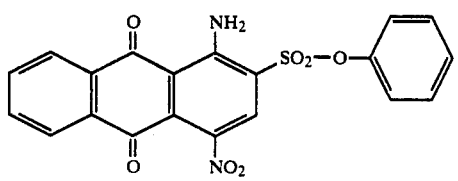

59 g of phenol and 47.5 g of dry potassium carbonate are introduced into 400 ccs of chlorobenzene, the mixture is heated to 100° C. and about 40 to 50 ccs of chlorobenzene are distilled off by applying a vacuum. After cooling the mixture to 25° C., 91.5 g of 1-amino-4-nitro-anthraquinone-2-sulphonic acid chloride (Example 1) are added. When the exothermic reaction has subsided, the mixture is stirred for a further 30 minutes and then diluted with 500 ccs of methanol and, after a further 30 minutes, the precipitate is filtered off. It is washed with methanol and then with water and dried at 60° C. Yield: 9.2 g, corresponding to 86% of theory.

Analysis: $C_{20}H_{12}N_2O_7S$ (424.4). Calculated: C 56.60; H 2.85; N 6.60; S 7.56. Found: C 56.5; H 2.7; N 6.3; S 7.7.

The potassium carbonate used as the acid-binding agent in the above example can also be replaced by sodium hydroxide, potassium hydroxide, calcium oxide, sodium carbonate, sodium bicarbonate, sodium acetate or potassium acetate. In this case, the sulphonic acid aryl ester can be obtained in a similarly good yield and purity. A similarly good yield and purity are also achieved with organic bases, with trimethylamine, triethylamine, pyridine or benzyltrimethyl-ammonium hydroxide.

If the chlorobenzene in the above example is replaced by the same amount of tetrahydrofurane, the same reaction product can be isolated in a similarly good yield and purity. Toluene, 1,2-dichlorobenzene, nitrobenzene, chloroform, 1,2-dichloroethane, dioxane, dimethylformamide, dimethylsulphoxide, sulpholane, pyridine, diglycol monomethyl ether, glycol dimethyl ether, acetone and methyl ethyl ketone can also be used as the solvent with the same success.

Reddish-tinged yellow shades with good fastness properties are achieved with the resulting dyestuff on synthetic fibre materials of cellulose esters, polyamides, polyurethanes, polyacrylonitriles and, in particular, polyesters.

EXAMPLES 23–120

The dyestuffs listed in Table 2, which give the shades indicated on woven fabrics or knitted fabrics of polyester fibres, triacetate fibres, polyamide fibres, polyurethane fibres or polyolefine fibres, are prepared analogously to that described in Example 22.

TABLE 2

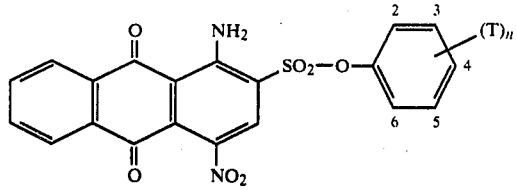

| Example No. | T | Colour shade |
|---|---|---|
| 23 | 2-$CH_3$ | yellow |
| 24 | 3-$CH_3$ | yellow |
| 25 | 4-$CH_3$ | yellow |
| 26 | 2,4-di-$CH_3$ | somewhat reddish-tinged yellow |
| 27 | 2-Cl | reddish-tinged yellow |
| 28 | 3-Cl | yellow |
| 29 | 4-Cl | yellow |
| 30 | 2,4-di-Cl | reddish-tinged yellow |
| 31 | 2,5-di-Cl | reddish-tinged yellow |
| 32 | 2,6-di-Cl | yellow |
| 33 | 2,4,5-tri-Cl | yellow |
| 34 | 2,4,6-tri-Cl | yellow |
| 35 | 2-$NO_2$ | reddish-tinged yellow |
| 36 | 3-$NO_2$ | reddish-tinged yellow |
| 37 | 4-$NO_2$ | reddish-tinged yellow |
| 38 | 2-$NO_2$—4-Cl | yellow |
| 39 | 3-$NO_2$—4-Cl | yellow |
| 40 | 2-Cl—5-$NO_2$ | yellow |
| 41 | 3-Cl—4-$NO_2$ | yellow |
| 42 | 2-$CH_3$—6-Cl | yellow |
| 43 | 2-$CH_3$—5-Cl | yellow |
| 44 | 2-$CH_3$—4-Cl | reddish-tinged yellow |
| 45 | 2-$CH_3$—5-$NO_2$ | yellow |
| 46 | 2-Cl—5-$CH_3$ | yellow |
| 47 | 3-$CH_3$—4-Cl | reddish-tinged yellow |
| 48 | 3-$CH_3$—4-$NO_2$ | yellow |
| 49 | 2-$C_2H_5$ | reddish-tinged yellow |
| 50 | 2,3-di-$CH_3$ | yellow |
| 51 | 3,4-di-$CH_3$ | yellow |
| 52 | 2,6-di-$CH_3$ | yellow |
| 53 | 3,5-di-$CH_3$ | yellow |
| 54 | 3,5-di-$CH_3$—4-Cl | yellow |
| 55 | 2,5-di-$CH_3$ | yellow |
| 56 | 2-isopropyl | reddish-tinged yellow |
| 57 | 3-$CH_3$—5-$C_2H_5$ | reddish-tinged yellow |
| 58 | 2,3,5-tri-$CH_3$ | yellow |
| 59 | 2-isobutyl | yellow |
| 60 | 2-tert.-butyl | yellow |
| 61 | 4-tert.-butyl | reddish-tinged yellow |
| 62 | 3-$CH_3$—5-isopropyl | reddish-tinged yellow |
| 63 | 4-isobutyl | reddish-tinged yellow |
| 64 | 4-isooctyl | yellow |
| 65 | 2,4-di-isobutyl | yellow |
| 66 | 2-cyclohexyl | yellow |
| 67 | 4-cyclohexyl | reddish-tinged yellow |

TABLE 2-continued

| | | |
|---|---|---|
| 68 | 4-cyclopentyl | reddished-tinged yellow |
| 69 | 2-phenyl | yellow |
| 70 | 3-phenyl | yellow |
| 71 | 4-phenyl | yellow |
| 72 | 2-bromo-4-phenyl | yellow |
| 73 | 2-benzyl | yellow |
| 74 | 4-benzyl | reddish-tinged yellow |
| 75 | 4-(2-phenyl-prop-2-yl)- | yellow |
| 76 | 2-OCH$_3$ | yellow |
| 77 | 3-OCH$_3$ | yellow |
| 78 | 4-OCH$_3$ | reddish-tinged yellow |
| 79 | 2-OC$_2$H$_5$ | yelloe |
| 80 | 4-OC$_2$H$_5$ | reddish-tinged yellow |
| 81 | 2-isopropoxy | yellow |
| 82 | 4-isopropoxy | reddish-tinged yellow |
| 83 | 4-n-butoxy | yellow |
| 84 | 3-F | yellow |
| 85 | 4-F | yellow |
| 86 | 3-CF$_3$ | yellow |
| 87 | 4-CF$_3$ | reddish-tinged yellow |
| 88 | 3-Br | yellow |
| 89 | 4-Br | reddish-tinged yellow |
| 90 | 4-OPh | reddish-tinged yellow |
| 91 | 4-O—cyclohexyl | reddish-tinged yellow |
| 92 | 3-CO—CH$_3$ | yellow |
| 93 | 4-CO—CH$_3$ | yellow |
| 94 | 4-CO—Ph | yellow |
| 95 | 3-COOCH$_3$ | yellow |
| 96 | 4-COOCH$_3$ | yellow |
| 97 | 3-COOH | yellow |
| 98 | 3-CN | yellow |
| 99 | 4-CN | reddish-tinged yellow |
| 100 | 4-SO$_2$—CH$_3$ | yellow |
| 101 | 4-SO$_2$—Ph | yellow |
| 102 | 4-SCH$_3$ | reddish-tinged yellow |
| 103 | 3-CH$_3$—4-SCH$_3$ | yellow |
| 104 | 2,6-di-CH$_3$—4-SCH$_3$ | yellow |

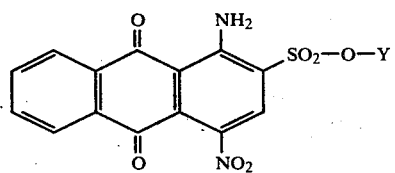

| Example No. | Y | Colour shade |
|---|---|---|
| 105 | (5,6,7,8-tetrahydronaphth-1-yl) | yellow |
| 106 | (5,6,7,8-tetrahydronaphth-2-yl) | yellow |
| 107 | (indan-5-yl) | yellow |
| 108 | (8-methyl-5,6,7,8-tetrahydronaphth-1-yl) | yellow |
| 109 | (4-chloronaphth-1-yl) | yellow |
| 110 | (naphth-1-yl) | reddish-tinged yellow |
| 111 | (naphth-2-yl) | reddish-tinged yellow |
| 112 | (4-methylnaphth-1-yl) | yellow |
| 113 | (5-methylnaphth-1-yl) | yellow |
| 114 | (5-chloronaphth-1-yl) | yellow |
| 115 | (4-bromonaphth-1-yl) | yellow |
| 116 | (6-methylnaphth-2-yl) | reddish-tinged yellow |
| 117 | (8-chloronaphth-2-yl) | yellow |
| 118 | (6-bromonaphth-2-yl) | yellow |
| 119 | (8-methylnaphth-2-yl) | yellow |
| 120 | (3-methyl-5,6,7,8-tetrahydronaphth-2-yl) | yellow |

EXAMPLE 121

A mixture of 40 ccs of chlorobenzene, 5.9 g of phenol and 4.75 g of dry potassium carbonate are partly distilled in vacuo (a few ccs of chlorobenzene are distilled off). After cooling the mixture to 25° C., 10.3 g of a mixture of 1-amino-4-nitro-6-chloro- and -7-chloro-anthraquinone-2-sulphonic acid chloride are introduced, whereupon the temperature rises by about 10° C. The reaction mixture is stirred for a further 30 minutes and then diluted with 50 ccs of methanol and, after 30 minutes, the precipitate is filtered off, washed with methanol and then with water and dried. Yield: 9.4 g, corresponding to 81% of theory. The reaction can also be carried out in excess phenol as the reaction medium instead of in chlorobenzene.

The dyestuff dyes polyethylene terephthalate fibres and cellulose triacetate fibres in reddish-tinged yellow shades. An equivalent yellow dyeing is obtained on a fabric of polycyclohexane-dimethylene terephthalate fibres.

EXAMPLES 122–140

The anthraquinone compounds listed in Table 3, which give the shades indicated on woven fabrics or knitted fabrics of polyester fibres, triacetate fibres, polyamide fibres, polyurethane fibres or polyolefine fibres, are obtained analogously to those described in Examples 22 and 121.

TABLE 3

![Structure: anthraquinone with NH2, SO2-O-Y, NO2, X1 at 5, X2 at 8]

| Example No. | Y | $X_1$ | $X_2$ | Colour shade |
|---|---|---|---|---|
| 122 | –C6H5 | 5-Cl | H | yellow |
| 123 | –C6H4–CH3 | 6-Cl | H | yellow |
| 124 | –C6H5 | 7-Cl | H | yellow |
| 125 | –C6H5 | 8-Cl | H | yellow |
| 126 | –naphthyl | 6-Cl | 7-Cl | yellow |
| 127 | –C6H5 | 6-Cl | 7-Cl | yellow |
| 128 | –C6H4–CH3 | 5-Cl | 8-Cl | yellow |
| 129 | –C6H4–OCH3 | 5-F | H | yellow |
| 130 | –C6H5 | 6-F | H | yellow |
| 131 | –C6H5 | 7-F | H | yellow |
| 132 | –C6H4–CH3 | 6-F | 7-F | yellow |
| 133 | –C6H5 | 6-Br | H | yellow |
| 135 | –C6H5 | 5-NO2 | H | yellow |
| 136 | –C6H4–CH3 | 5-NO2 | H | yellow |
| 137 | –C6H4–Cl | 5-NO2 | H | yellow |

TABLE 3-continued

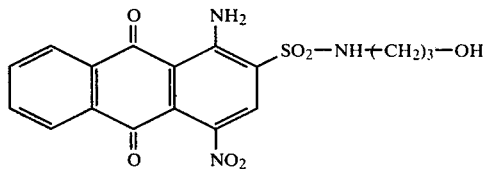

| Example No. | Y | $X_1$ | $X_2$ | Colour shade |
|---|---|---|---|---|
| 138 | CH3–C6H4– | 6-NO2 | H | yellow |
| 139 | –C6H5 | 7-NO2 | H | yellow |
| 140 | OCH3–C6H4– | 7-NO2 | H | yellow |

EXAMPLE 141

![Structure: 1-amino-4-nitro-anthraquinone-2-sulphonamide with SO2-NH-(CH2)3-OH]

91.5 g of 1-amino-4-nitro-anthraquinone-2-sulphonic acid chloride (preparation, for example, according to Example 1) are introduced into 300 ccs of chlorobenzene, and 46.9 g of 3-hydroxy-propylamine are added dropwise, whilst stirring, in a manner such that the temperature does not exceed 30° C. After 30 minutes, the reaction mixture is diluted with 500 ccs of methanol and, after a further 30 minutes, the precipitate is filtered off, washed with methanol and then with water and dried at 60° C. Yield: 81 g, corresponding to 80% of theory.

Analysis: $C_{17}H_{15}N_3O_7S$ (405.4). Calculated: C 50.37; H 3.73; N 10.37; S 7.91. Found: C 50.5; H 3.8; N 10.6; 7.9.

If the chlorobenzene in the above example is replaced by the same amount of toluene, the same reaction product can be isolated in a similarly good yield and purity. 1,2-Dichlorobenzene, nitrobenzene, chloroform, 1,2-dichloroethane, dioxane, tetrahydrofurane, dimethylformamide, dimethylsulphoxide, sulpholane, pyridine, diglycol monomethyl ether, glycol monomethyl ether, glycol dimethyl ether, acetone and methyl ethyl ketone can also be used as the solvent with the same success.

Instead of carrying out the reaction with excess amine, it can also be carried out with slightly more than the stoichiometrically required amount of amine in the presence of an acid-binding agent, for example according to the following instructions:

2.1 g of 3-hydroxy-propylamine and 2.6 g of dry potassium carbonate are introduced into 40 ccs of 1,2-dichlorobenzene, and 9.15 g of 1-amino-4-nitroanthraquinone-2-sulphonic acid chloride are then added in a manner such that the temperature does not exceed 30° C. After 30 minutes, the reaction mixture is diluted with 40 ccs of methanol and, after a further 30 minutes, the precipitate is filtered off, washed with methanol and water and dried at 60° C. Yield: 8.0 g, corresponding to 79% of theory, of the same product as above.

If the potassium carbonate used as the acid-binding agent in the above example is replaced by sodium carbonate, sodium bicarbonate, sodium hydroxide, calcium oxide, magnesium oxide, sodium acetate or potassium acetate, the sulphonamide can be obtained in a similarly good yield and purity. Similarly good results are also achieved with the organic bases trimethylamine, triethylamine, pyridine or benzyltrimethyl-ammonium hydroxide.

Reddish-tinged yellow to orange shades with good fastness properties are achieved with the dyestuff, prepared according to one of the above sets of instructions, on synthetic fibre materials of cellulose esters, polyamides, polyurethanes, polyacrylonitriles and, in particular, polyesters.

EXAMPLE 142

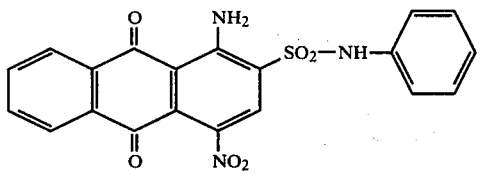

46.5 g of aniline are added to a suspension of 73.3 g of 1-amino-4-nitro-anthraquinone-2-sulphonic acid chloride in 240 ccs of 1,2-dichloro-benzene in a manner such that the temperature does not exceed 30° C. After stirring the reaction mixture at room temperature for 1 hour, it is diluted with 400 ccs of methanol and stirred for a further 30 minutes and the precipitate is filtered off, washed with methanol and then with water and dried at 60° C. Yield: 73.2 g, corresponding to 86% of theory.

The reaction proceeds just as smoothly in chlorobenzene or toluene as the solvent, and gives the product in virtually the same yield and purity.

On synthetic fibre materials of cellulose esters, polyamides, polyurethanes, polyacrylonitriles and, in particular, polyesters, the dyestuff gives reddish-tinged yellow to orange shades with good fastness properties.

EXAMPLES 143–333

The anthraquinone compounds listed in Table 4, which give the shades indicated on woven fabrics or knitted fabrics of polyester fibres, polyamide fibres, polyurethane fibres or polyolefine fibres, are prepared analogously to those described in Examples 141 and 142.

TABLE 4

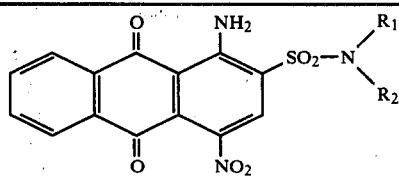

| Example No. | $R_1$ | $R_2$ | Colour shade |
|---|---|---|---|
| 143 | H | H | reddish-tinged yellow |
| 144 | $CH_3$ | H | deeply reddish-tinged yellow |
| 145 | $CH_3$ | $CH_3$ | reddish-tinged yellow |
| 146 | $C_2H_5$ | H | reddish-tinged yellow |
| 147 | $C_2H_5$ | $C_2H_5$ | reddish-tinged yellow |
| 148 | n-$C_3H_7$ | H | orange |
| 149 | n-$C_3H_7$ | n-$C_3H_7$ | reddish-tinged yellow |
| 150 | i-$C_3H_7$ | H | orange |
| 151 | i-$C_3H_7$ | i-$C_3H_7$ | orange |
| 152 | n-$C_4H_9$ | H | orange |
| 153 | n-$C_4H_9$ | n-$C_4H_9$ | reddish-tinged yellow |
| 154 | $CH_3$\\$C_2H_5$/CH— | H | reddish-tinged yellow |
| 155 | $(CH_3)_2CH-CH_2-$ | H | orange |
| 156 | $(CH_3)_3C-$ | H | orange |
| 157 | $CH_3-CH_2-C(CH_3)_2-$ | H | orange |
| 158 | $CH_3\text{-}(CH_2)_5-$ | H | reddish-tinged yellow |
| 159 | $CH_3\text{-}(CH_2)_3-CH(C_2H_5)-CH_2-$ | H | reddish-tinged yellow |
| 160 | $CH_3\text{-}(CH_2)_9-$ | H | orange |
| 161 | $Cl-CH_2-CH_2-$ | H | orange |
| 162 | $H_2N-CH_2-CH_2-$ | H | orange |
| 163 | $CH_3NH-CH_2-CH_2-$ | $CH_3$ | orange |
| 164 | $(C_2H_5)_2N\text{-}(CH_2)_2-$ | H | reddish-tinged yellow |
| 165 | $CH_3-NH-(CH_2)_3-$ | H | reddish-tinged yellow |
| 166 | $(CH_3)_2N-(CH_2)_3$ | H | orange |
| 167 | $(C_2H_5)_2N-(CH_2)_3-$ | H | reddish-tinged yellow |
| 168 | $(C_4H_9)_2N-(CH_2)_3-$ | H | reddish-tinged yellow |
| 169 | $HO-(CH_2)_2-$ | H | reddish-tinged yellow |
| 170 | $CH_3O-(CH_2)_2-$ | H | orange |
| 171 | $HO-(CH_2)_2-$ | $CH_3$ | reddish-tinged yellow |
| 172 | $HO-(CH_2)_2-$ | $HO-(CH_2)_2-$ | orange |
| 173 | $HO-(CH_2)_3-$ | $CH_3$ | orange |

TABLE 4-continued

| | | | |
|---|---|---|---|
| 174 | CH₃O—(CH₂)₃— | H | orange |
| 175 | C₂H₅—O—(CH₂)₃— | H | orange |
| 176 | C₄H₉—O—(CH₂)₃— | H | orange |
| 177 | CH₃—CH(OH)—CH₂— | H | reddish-tinged yellow |
| 178 | CH₃—CH(OH)—CH₂— | CH₃—CH(OH)—CH₂— | orange |
| 179 | CH₃—CH(OH)—(CH₂)₂— | H | orange |
| 180 | HO—CH₂—C(CH₃)₂— | H | orange |
| 181 | CH₃O—CO—CH₂— | H | orange |
| 182 | CH₃O—CO—CH₂— | CH₃ | reddish-tinged yellow |
| 183 | CH₃O—CO—(CH₂)₂— | H | reddish-tinged yellow |
| 184 | NC—(CH₂)₂— | CH₃ | reddish-tinged yellow |
| 185 | C₄H₉O—CO—CH₂— | H | orange |
| 186 | NC—(CH₂)₅— | H | reddish-tinged yellow |
| 187 | CH₃O—CO—(CH₂)₁₀— | H | reddish-tinged yellow |
| 188 |  | H | reddish-tinged yellow |
| 189 |  | CH₃ | orange |
| 190 |  | C₂H₅ | orange |
| 191 |  |  | orange |
| 192 |  | HO—(CH₂)₂— | reddish-tinged yellow |
| 193 |  | H | reddish-tinged yellow |
| 194 |  | H | orange |
| 195 |  | H | orange |
| 196 |  | H | reddish-tinged yellow |
| 197 |  | H | reddish-tinged yellow |
| 198 |  | H | reddish-tinged yellow |
| 199 |  | H | orange |
| 200 |  | H | orange |
| 201 |  | H | orange |
| 202 |  | H | orange |
| 203 |  | H | orange |
| 204 |  | H | orange |
| 205 |  | H | orange |
| 206 |  | H | orange |
| 207 |  | H | reddish-tinged yellow |

TABLE 4-continued

| | | | |
|---|---|---|---|
| 208 |  | H | orange |
| 209 | 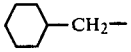 | H | reddish-tinged yellow |
| 210 | 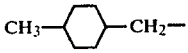 | H | orange |
| 211 | 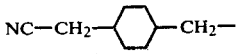 | H | orange |
| 212 | 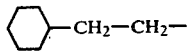 | H | orange |
| 213 | 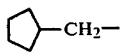 | H | orange |
| 214 | 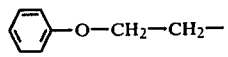 | H | reddish-tinged yellow |
| 215 | 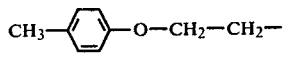 | H | orange |
| 216 |  | H | orange |
| 217 | C₄H₉—NH—CH₂—CH₂— | H | reddish-tinged yellow |
| 218 | CF₃ | H | orange |
| 219 | 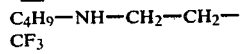 | H | orange |
| 220 |  | CH₃ | reddish-tinged yellow |
| 221 | 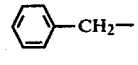 | H | reddish-tinged yellow |
| 222 | 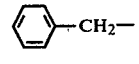 | H | reddish-tinged yellow |
| 223 |  | H | reddish-tinged yellow |
| 224 |  | H | orange |
| 225 | 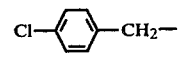 | H | reddish-tinged yellow |
| 226 | 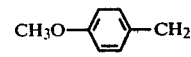 | H | orange |
| 227 | 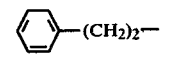 | H | orange |
| 228 | 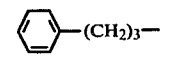 | H | orange |
| 229 | 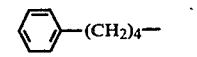 | H | orange |
| 230 | 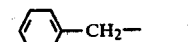 | H | reddish-tinged yellow |
| 231 |  | H | reddish-tinged yellow |
| 232 | 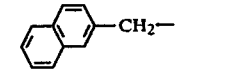 | H | orange |

TABLE 4-continued

| | | | |
|---|---|---|---|
| 233 | (2,4,6-tri-CH3-benzyl) CH3-C6H2(CH3)2-CH2— | H | orange |
| 234 | C6H5— | CH3 | orange |
| 235 | C6H5— | C2H5 | orange |
| 236 | C6H5— | n-C4H9 | reddish-tinged yellow |
| 237 | C6H5— | —CH2—CH2—OH | orange |
| 238 | 3-CH3-C6H4— | n-C4H9— | orange |
| 239 | 3-CH3-C6H4— | —CH2—CH2—OH | orange |

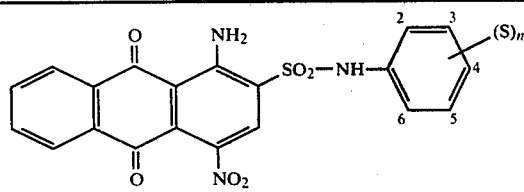

| Example No. | (S)$_n$ | Colour shade |
|---|---|---|
| 240 | 2-Cl | orange |
| 241 | 3-Cl | orange |
| 242 | 4-Cl | orange |
| 243 | 3,4-Di-Cl | reddish-tinged yellow |
| 244 | 3,5-Di-Cl | reddish-tinged yellow |
| 245 | 2-F | reddish-tinged yellow |
| 246 | 3-F | reddish-tinged yellow |
| 247 | 4-F | orange |
| 248 | 4-Br | orange |
| 249 | 3-NO2 | orange |
| 250 | 4-NO2 | orange |
| 251 | 3-CF3 | orange |
| 252 | 4-CF3 | reddish-tinged yellow |
| 253 | 2-CH3 | reddish-tinged yellow |
| 254 | 3-CH3 | orange |
| 255 | 4-CH3 | orange |
| 256 | 2-CH3—5-Cl | orange |
| 257 | 3-CH3—4-Cl | reddish-tinged yellow |
| 258 | 2-Cl—5-CF3 | orange |
| 259 | 2,4-Di-Cl—5-CH3 | orange |
| 260 | 3-Cl—4-CH3 | orange |
| 261 | 2-C2H5 | reddish-tinged yellow |
| 262 | 4-C2H5 | reddish-tinged yellow |
| 263 | 3,4-Di-CH3 | orange |
| 264 | 2,4-Di-CH3 | reddish-tinged yellow |
| 265 | 3,5-Di-CH3 | reddish-tinged yellow |
| 266 | 3,5-Di-CF3 | orange |
| 267 | 2,5-Di-CH3 | orange |
| 268 | 2,4,5-Tri-CH3 | reddish-tinged yellow |
| 269 | 4-tert.-Butyl | orange |
| 270 | 4-Cyclopentyl | orange |
| 271 | 4-Cyclohexyl | orange |
| 272 | 2-CH3—4-cyclohexyl | reddish-tinged yellow |
| 273 | 4-Phenyl | orange |
| 274 | 3-N(CH3)2 | orange |
| 275 | 3-NH—CO—CH3 | orange |
| 276 | 4-N(CH3)2 | orange |
| 277 | 4-N(C2H5)2 | reddish-tinged yellow |
| 278 | 4-NH—C6H5 | reddish-tinged yellow |
| 279 | 2-OCH3 | reddish-tinged yellow |

TABLE 4-continued

| | | |
|---|---|---|
| 280 | 2-OC$_2$H$_5$ | orange |
| 281 | 2-O—<phenyl> | reddish-tinged yellow |
| 282 | 2-OCH$_3$—5-Cl | reddish-tinged yellow |
| 283 | 3-OH | orange |
| 284 | 3-OCH$_3$ | orange |
| 285 | 3-OC$_2$H$_5$ | reddish-tinged yellow |
| 286 | 4-OH | reddish-tinged yellow |
| 287 | 4-OCH$_3$ | reddish-tinged yellow |
| 288 | 4-OC$_2$H$_5$ | reddish-tinged yellow |
| 289 | 4-O—(CH$_2$)$_2$—OH | orange |
| 290 | 4-OC$_4$H$_9$ | reddish-tinged yellow |
| 291 | 4-NH—<phenyl>—OCH$_3$ | reddish-tinged yellow |
| 292 | 4-SO$_2$—CH$_3$ | orange |
| 293 | 3-OH—4-CH$_3$ | reddish-tinged yellow |
| 294 | 3-OCH$_3$—4-CH$_3$ | orange |
| 295 | 2-CH$_3$—4-OCH$_3$ | reddish-tinged yellow |
| 296 | 2-CH$_3$—5-OCH$_3$ | orange |
| 297 | 2-OCH$_3$—4-Cl—5-CH$_3$ | reddish-tinged yellow |
| 298 | 2-(SO$_2$—C$_2$H$_5$)—5-CF$_3$ | orange |
| 299 | 2,4-Di-OCH$_3$ | reddish-tinged yellow |
| 300 | 2,5-Di-OCH$_3$ | reddish-tinged yellow |
| 301 | 2,5-Di-OC$_2$H$_5$ | reddish-tinged yellow |
| 302 | 2-OCH$_3$—5-(SO$_2$—CH$_3$) | orange |
| 303 | 2-COOH | reddish-tinged yellow |
| 304 | 3-COOH | orange |
| 305 | 2-COOCH$_3$ | orange |
| 306 | 2-COOC$_2$H$_5$ | orange |
| 307 | 2-CO—NH$_2$ | reddish-tinged yellow |
| 308 | 3-CN | orange |
| 309 | 4-COOH | orange |
| 310 | 4-COOC$_2$H$_5$ | orange |
| 311 | 4-CO—NH$_2$ | reddish-tinged yellow |
| 312 | 3,4-Di-CN | orange |
| 313 | 2,4-Di-CN | orange |
| 314 | 3-SO$_2$NH$_2$ | reddish-tinged yellow |
| 315 | 3-SO$_2$—NH—(CH$_2$)$_2$—OH | orange |
| 316 | 4-CO—CH$_3$ | reddish-tinged yellow |
| 317 | 4-CO—<phenyl> | reddish-tinged yellow |

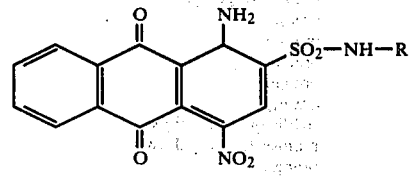

| Example No. | R | Colour shade |
|---|---|---|
| 318 | <1-naphthyl> | orange |
| 319 | <4-methyl-1-naphthyl> | orange |
| 320 | <6-methyl-2-naphthyl> | orange |
| 321 | <4-chloro-1-naphthyl> | reddish-tinged yellow |
| 322 | <4-bromo-1-naphthyl> | reddish-tinged yellow |

TABLE 4-continued

| No. | Structure | Colour shade |
|---|---|---|
| 323 | naphthyl-OC₂H₅ | reddish-tinged yellow |
| 324 | naphthyl | orange |
| 325 | CH₃-naphthyl | orange |
| 326 | Cl-naphthyl | orange |
| 327 | HO-naphthyl | orange |
| 328 | tetrahydronaphthyl | orange |
| 329 | CH₃-tetrahydronaphthyl | orange |
| 330 | tetrahydronaphthyl | reddish-tinged yellow |

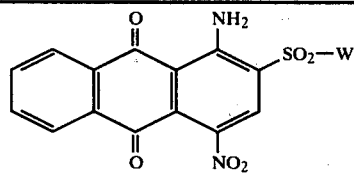

| Example No. | W | Colour shade |
|---|---|---|
| 331 | —N(pyrrolidinyl) | orange |
| 332 | —N(piperidinyl) | orange |
| 333 | —N(morpholinyl) | orange |

EXAMPLE 334

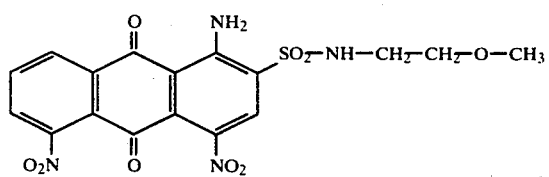

3.3 g of 2-methoxyethyl-amine are added dropwise to a mixture of 8.2 g of 1-amino-4,5-dinitro-anthraquinone-2-sulphonic acid chloride and 30 ccs of dry acetone in a manner such that the temperature does not rise above 30° C. After 30 minutes at room temperature, the reaction mixture is diluted with 30 ccs of methanol and stirred for a further 30 minutes and the precipitate is then filtered off, washed with methanol and water and dried at 60° C. Yield: 8.1 g, corresponding to 90% of theory.

The reaction proceeds just as smoothly in toluene or chlorobenzene as the solvent, and gives the product in virtually the same yield and purity.

On synthetic fibre materials of cellulose esters, polyamides, polyurethanes, polyacrylonitriles and, in particular, polyesters, the dyestuff gives yellow shades with good fastness properties.

EXAMPLES 335–363

The anthraquinone compounds listed in Table 5, which give the shades indicated on woven fabrics or knitted fabrics of polyester fibres, polyamide fibres, polyurethane fibres or polyolefine fibres, are prepared analogously to those described in Examples 141, 142 and 334.

TABLE 5

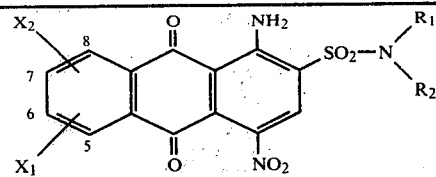

| Example No. | $R_1$ | $R_2$ | $X_1$ | $X_2$ | Colour shade |
|---|---|---|---|---|---|
| 335 | H | H | 5-Cl | H | orange |
| 336 | —C$_6$H$_5$ | H | 5-Cl | H | orange |
| 337 | —C$_2$H$_5$ | —C$_2$H$_5$ | 6-Cl | H | reddish-tinged orange |
| 338 | —C$_6$H$_4$—Cl | H | 6-Cl | H | orange |
| 339 | —(CH$_2$)$_3$—OCH$_3$ | H | 7-Cl | H | orange |
| 340 | —C$_6$H$_5$ | H | 7-Cl | H | orange |
| 341 | —C$_4$H$_9$ | H | 8-Cl | H | orange |
| 342 | —C$_6$H$_4$—CH$_3$ | H | 8-Cl | H | reddish-tinged orange |
| 343 | —CH$_2$—CH$_2$—OH | H | 6-Cl | 7-Cl | orange |
| 344 | —C$_6$H$_4$—CH$_3$ | H | 6-Cl | 7-Cl | orange |
| 345 | —C$_6$H$_4$—CF$_3$ | H | 6-Cl | 7-Cl | orange |
| 346 | —CH$_2$—C$_6$H$_5$ | H | 5-Cl | 8-Cl | orange |
| 347 | —(CH$_2$)$_2$—OCH$_3$ | H | 5-Cl | 8-Cl | orange |
| 348 | —C$_6$H$_5$ | H | 5-Cl | 8-Cl | orange |
| 349 | —C$_6$H$_{11}$ | H | 5-F | H | orange |
| 350 | —CH$_2$—C$_6$H$_5$ | H | 5-F | H | reddish-tinged orange |
| 351 | —(CH$_2$)$_3$—OC$_2$H$_5$ | H | 6-F | H | orange |
| 352 | —C$_6$H$_5$ | H | 6-F | H | orange |
| 353 | —CH$_2$—CH$_2$—OH | H | 7-F | H | reddish-tinged orange |
| 354 | —C$_6$H$_4$—CH$_3$ | H | 7-F | H | reddish-tinged orange |
| 355 | —(CH$_2$)$_3$—OH | H | 8-F | H | orange |
| 356 | —CH$_2$—CH$_2$—OCH$_3$ | H | 6-F | 7-F | orange |
| 357 | —(CH$_2$)$_3$—OCH$_3$ | H | 5-NO$_2$ | H | yellow |
| 358 | —C$_6$H$_4$—CH$_3$ | H | 5-NO$_2$ | H | yellow |
| 359 | —CH$_3$ | CH$_3$ | 6-NO$_2$ | H | yellow |
| 360 | —C$_6$H$_5$ | H | 6-NO$_2$ | H | yellow |
| 361 | —C$_6$H$_{11}$ | H | 7-NO$_2$ | H | yellow |
| 362 | —C$_6$H$_4$—CH$_3$ | H | 8-NO$_2$ | H | yellow |
| 363 | —C$_{10}$H$_7$ | H | 5-NO$_2$ | H | yellow |

DYEING EXAMPLES

EXAMPLE 364

100 g of polyethylene terephthalate fibres are dyed with 1 g of the dyestuff of Example 22, which has first been brought into a finely divided form in the presence of dispersing agents, in 4 l of water in the presence of 15 g of o-cresotic acid methyl ester, as a carrier, at 100° C. and at pH 4.5 for 2 hours. A reddish-tinged yellow dyeing which is distinguished by good fastness to washing, heat-setting, rubbing and light is obtained. A similar dyeing is obtained if polyester fibres of 1,4-bis-(hydroxymethyl)-cyclohexane and terephthalic acid are used as the polyester fibres.

The dyeing can likewise also be carried out with the dyestuffs obtained according to Example 23 to 140.

EXAMPLE 365

10 g of polyethylene glycol terephthalate hank material are dyed in a liquor of 600 ccs of water, 0.1 g of the dyestuff of Example 141, present in the finely divided form, 3.4 g of a mixture of o-, m- and p-cresotic acid methyl ester and 0.6 g of a mixture of equal parts of an aralkylsulphonate and a non-ionic polyglycol ether, after adding sulphuric acid until a pH value of 4.5 is established, at 96° to 98° C. for 2 hours. The hank material is then rinsed and dried. The fastness to rubbing can be improved if the hank material is after-treated for 10 to 30 minutes in a simmering bath which contains, per 1,000 ccs of water, 5.5 g of sodium hydroxide solution of °Bé strength 38, 2 g of sodium dithionite and 1 g of a polyglycol ether of a fatty acid amide. An orange dyeing with good fastness properties, in particular a very good fastness to sublimation, is obtained.

The dyeing can likewise also be carried out with the dyestuffs obtained according to Examples 22–140 and 142 to 363.

EXAMPLE 366

100 g of polyester fibres (polyethylene terephthalate) are dyed with 1 g of the dyestuff given in Example 25, which has first been brought into a finely divided form with the customary auxiliaries, in 3 l of water at 125°–130° C. under pressure for 1 hour. A yellow dyeing with good fastness properties is obtained.

The dyeing can likewise also be carried out with the dyestuffs obtained according to Examples 22 to 24 and 26 to 140.

EXAMPLE 367

10 g of a polyethylene glycol terephthalate fabric are dyed in a liquor of pH 4.5 consisting of 400 ccs of water and 0.1 g of the dyestuff of Example 142, present in a very finely divided form, and 0.3 g of a mixture of equal parts of an aralkylsulphonate and a non-ionic polyglycol ether, at 120° to 130° for 2 hours. After rinsing and drying the fabric, a reddish-tinged yellow dyeing with good to very good fastness properties, in particular a very good fastness to sublimation, is obtained. The dyeing can likewise also be carried out with the dyestuffs obtained according to Examples 22 to 141 and 143 to 363.

EXAMPLE 368

20 g of cellulose 2½-acetate fibres are dyed in a liquor consisting of 600 ml of water, 1 g of Marseilles soap and 0.2 g of the dyestuff given in Example 172, brought into a finely divided form, at 75° C. for 1 hour. An orange dyeing with good fastness to rubbing, light and washing is obtained.

The dyeing can likewise also be carried out with the other dyestuffs mentioned.

EXAMPLE 369

A dyebath, in which 100 g of cellulose triacetate fibres are dyed at 100° C. for 1 hour, is prepared using 1 g of the dyestuff from Example 61, which has first been brought into a finely divided form using the auxiliaries customary for this purpose, 6 g of a fatty alcohol sulphonate and 3 l of water. A reddish-tinged yellow dyeing with very good fastness to washing, heat-setting, rubbing and light is obtained.

The dyeing can likewise also be carried out with the other dyestuffs mentioned.

EXAMPLE 370

100 g of polyamide fabric are dyed with 1 g of the dyestuff given in Example 171, which has first been brought into a finely divided form by customary methods, in 4 l of water at 100° C. for 1 hour. The fabric is then rinsed whilst warm and in the cold and dried. A reddish-tinged yellow dyeing with good fastness properties is obtained. Instead of polyamide fibres, polyurethane fibres can be used with the same success.

The dyeing can likewise also be carried out with the other dyestuffs mentioned.

EXAMPLE 371

A polyester fibre (polyethylene terephthalate) fabric is impregnated, on a padder, with a liquor which contains, per liter, 20 g of the dyestuff of Example 174, which has first been brought into a finely divided form in the presence of dispersing agents. The fabric is squeezed off to a weight increase of 70% and dried at 80°–120° C. in a tensionless nozzle-type drier or drying cabinet. The fabric is then treated with hot air in a stenter or nozzle hot-flue at 190°–220° C. for about 45 seconds and thereafter rinsed, subjected to a reductive after-treatment, if appropriate, and washed, rinsed and dried. The reductive after-treatment for the purpose of removing portions of the dyestuff adhering to the surface of the fibres can be carried out by introducing the fabric, at 25° C., into a liquor containing 3–5 cm$^3$/l of sodium hydroxide solution of °Bé strength 38 and 1–2 g/l of sodium dithionite (concentrated), heating the bath to 70° C. in the course of about 15 minutes and leaving it at 70° C. for a further 10 minutes. The fibres are then rinsed whilst hot, acidified with 2—3 cm$^3$/l of 85% strength formic acid at 50° C., rinsed and dried. An orange dyeing which is distinguished by good fastness properties is obtained.

A similar dyeing is obtained if polyester fibres of 1,4-bis-(hydroxymethyl)-cyclohexane and terephthalic acid are used instead of polyethylene terephthalate fibres. A reddish-tinged yellow dyeing is obtained in a similar manner if cellulose triacetate fibres are employed instead of polyethylene terephthalate fibres and the thermosol process is carried out at 215° C., or if polyamide fibres or polyurethane fibres are used and the thermosol process is carried out at 190°–215° C.

The dyeing can likewise also be carried out with the dyestuffs obtained according to Examples 22 to 173 and 175 to 363.

EXAMPLE 372

A scoured and heat-set fabric of polyethylene terephthalate is printed with a paste consisting of the following components: 20 g of the dyestuff obtained according to Example 142, in a finely divided form, 520 g of water, 450 g of crystal gum, 1:2, and 10 g of cresotic acid methyl ester. Instead of crystal gum, it is also possible to use an alginate thickener. In order to fix the dyestuff, the printed and dried goods are treated with hot air at 200° C. or passed over a high-capacity stenter at 190°–220° C. or through a condensation apparatus. The treatment time is 30–60 seconds. The resulting fixed print is then rinsed in the cold, soaped with 1–2 g/l of an anionic washing agent at 70°–80° C. for about 10 minutes, rinsed, first whilst hot and then in the cold, and dried. A clear orange-coloured print with good fastness properties is obtained.

A reddish-tinged yellow print is obtained in a similar manner if cellulose triacetate fibres, polyamide fibres or polyurethane fibres are employed instead of polyethylene terephthalate fibres.

The dyeing can likewise also be carried out with the dyestuffs obtained according to Examples 22 to 141 and 143 to 363.

We claim:

1. Anthraquinone dyestuffs of the formula

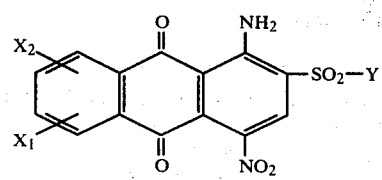

in which

Y denotes a group of the formulae —O—R or

R denotes optionally substituted aryl, $R_1$ and $R_2$ denote hydrogen or optionally substituted alkyl, cycloalkyl, aralkyl or aryl, or, together with the bonding nitrogen atom, a ring and $X_1$ and $X_2$ denote hydrogen, halogen or nitro.

2. Anthraquinone dyestuffs of the formula

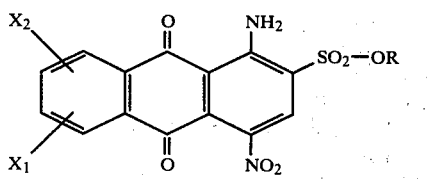

in which R, $X_1$ and $X_2$ have the meaning indicated in claim 1.

3. Anthraquinone dyestuffs according to claim 2, characterised in that R denotes a phenyl radical which is substituted by 1 to 3 radicals from the series $C_1$- to $C_4$-alkyl, $C_1$- to $C_4$-alkoxy, halogen, such as, in particular, fluorine, chlorine or bromine, methylmercapto, nitro, trifluoromethyl, $C_5$- to $C_6$-cycloalkyl, phenyl, acetyl, benzoyl, carbomethoxy or carboxyl or a naphthyl radical or 5,6,7,8-tetrahydronaphthyl radical which is optionally substituted by methyl, chlorine or bromine.

4. Anthraquinone dyestuffs of the formula

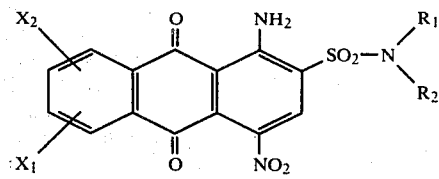

in which $R_1$, $R_2$, $X_1$ and $X_2$ have the meaning indicated in claim 1.

5. Anthraquinone dyestuffs according to claim 4, characterised in that $R_1$ and $R_2$ denote hydrogen, $C_1$- to $C_6$-alkyl which is optionally substituted by hydroxyl, $C_1$- to $C_4$-alkoxy, cyano or cyclohexyl, cyclohexyl which is optionally substituted by 1 to 3 methyl radicals or by cyano, benzyl, phenethyl or naphthylmethyl, optionally monosubstituted, disubstituted or trisubstituted by halogen, methyl or methoxy, phenyl which is substituted by 1 to 3 radicals from the series $C_1$- to $C_4$-alkyl, $C_1$- to $C_4$-alkoxy, chlorine, fluorine, bromine, nitro, trifluoromethyl, $C_5$- to $C_6$-cycloalkyl, phenyl or acetyl, or naphthyl or 5,6,7,8-tetrahydronaphthyl, optionally substituted by methyl, chlorine or bromine, and those in which $R_1$ and $R_2$, together with the bonding nitrogen atom, represent —(CH$_2$)$_4$—, —(CH$_2$)$_5$— or —(CH$_2$)$_2$—O—(CH$_2$)$_2$—.

6. Anthraquinone dyestuffs according to claim 4 or 5, characterised in that $R_1$ represents hydrogen.

7. The anthraquinone dyestuff of the formula

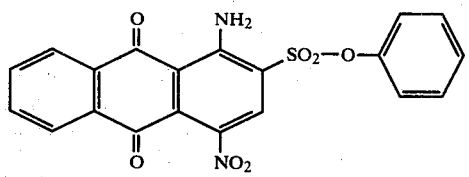

8. The anthraquinone dyestuff of the formula

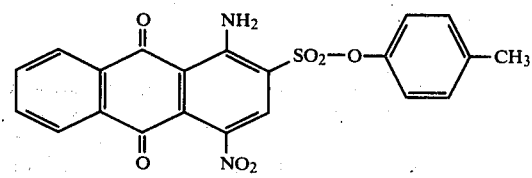

9. The anthraquinone dyestuff of the formula

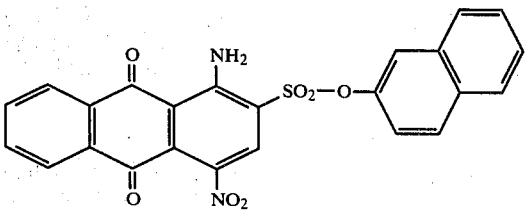

10. The anthraquinone dyestuff of the formula

11. The anthraquinone dyestuff of the formula
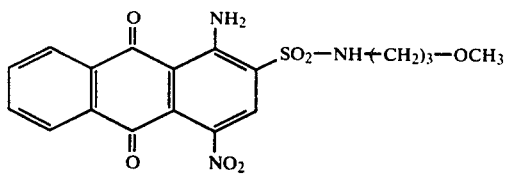
12. The anthraquinone dyestuff of the formula
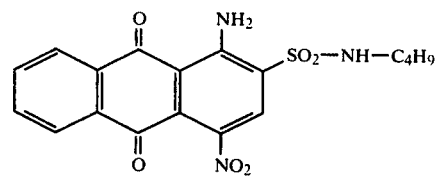
13. The anthraquinone dyestuff of the formula
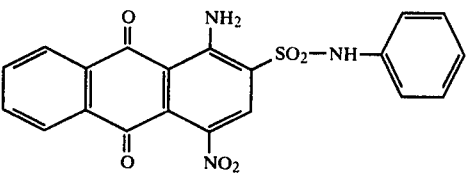
* * * * *